(12) United States Patent
Kelch et al.

(10) Patent No.: US 9,133,975 B2
(45) Date of Patent: Sep. 15, 2015

(54) DEVICE AND PROCESS FOR THE OUTPUT OF MEDICAL DATA

(75) Inventors: Jürgen Kelch, Bad Schwartau (DE); Gerald Panitz, Klenzau (DE); Volker Schierschke, Lübeck (DE)

(73) Assignee: Dräger Medical GmbH, Lübeck (DE)

( * ) Notice: Subject to any disclaimer, the term of this patent is extended or adjusted under 35 U.S.C. 154(b) by 1753 days.

(21) Appl. No.: 12/188,374

(22) Filed: Aug. 8, 2008

(65) Prior Publication Data

US 2009/0105551 A1 Apr. 23, 2009

(30) Foreign Application Priority Data

Oct. 19, 2007 (DE) .......................... 10 2007 050 060

(51) Int. Cl.
| | |
|---|---|
| A61B 5/00 | (2006.01) |
| F16M 11/12 | (2006.01) |
| F16M 11/04 | (2006.01) |
| F16M 11/14 | (2006.01) |
| F16M 11/18 | (2006.01) |
| F16M 11/20 | (2006.01) |
| F16M 13/02 | (2006.01) |

(52) U.S. Cl.
CPC .............. *F16M 11/12* (2013.01); *A61B 5/742* (2013.01); *F16M 11/04* (2013.01); *F16M 11/14* (2013.01); *F16M 11/18* (2013.01); *F16M 11/2021* (2013.01); *F16M 11/2078* (2013.01); *F16M 13/02* (2013.01); *A61B 5/00* (2013.01); *A61B 2560/0242* (2013.01); *F16M 2200/044* (2013.01)

(58) Field of Classification Search
None
See application file for complete search history.

(56) References Cited

U.S. PATENT DOCUMENTS

| | | | | |
|---|---|---|---|---|
| 6,015,120 | A  * | 1/2000 | Sweere et al. | ............ 248/123.11 |
| 6,020,890 | A  * | 2/2000 | Kohda | .......... 345/419 |
| 6,131,874 | A | 10/2000 | Vance et al. | |
| 6,864,912 | B1 * | 3/2005 | Mahaffey et al. | .............. 348/61 |
| 7,154,397 | B2 * | 12/2006 | Zerhusen et al. | .......... 340/573.1 |
| 7,369,672 | B2 * | 5/2008 | Hirschhorn | .................... 381/333 |
| 7,557,718 | B2 * | 7/2009 | Petrosenko et al. | ........ 340/573.1 |
| 7,630,193 | B2 * | 12/2009 | Ledbetter et al. | ........ 361/679.21 |
| 7,688,211 | B2 * | 3/2010 | Borovoy et al. | .......... 340/573.1 |
| 7,851,736 | B2 | 12/2010 | Spahn | |
| 8,010,180 | B2 * | 8/2011 | Quaid et al. | .................. 600/424 |
| 8,462,103 | B1 * | 6/2013 | Moscovitch et al. | ......... 345/156 |
| 2002/0149613 | A1 * | 10/2002 | Gutta et al. | ................... 345/728 |
| 2002/0196141 | A1 * | 12/2002 | Boone et al. | .................. 340/540 |
| 2004/0148197 | A1 * | 7/2004 | Kerr et al. | ......................... 705/2 |

(Continued)

FOREIGN PATENT DOCUMENTS

| | | |
|---|---|---|
| DE | 102 53 785 A1 | 6/2004 |
| DE | 10 2006 011 233 A1 | 9/2007 |
| WO | 01/13337 A1 | 2/2001 |

*Primary Examiner* — William Thomson
*Assistant Examiner* — Bobby Soriano
(74) *Attorney, Agent, or Firm* — McGlew and Tuttle, P.C.

(57) ABSTRACT

A device is provided for the output of medical data with an output device (1) for the output of medical data in a first output mode or in a second output mode different therefrom. The device includes a detection device (3, 4) for detecting an ambient parameter and an automatic switchover device for the output of medical data in the first output mode if the ambient parameter detected by the detection device is in a first range of values, and for the output of medical data in a second output mode if the ambient parameter detected by the detection device is in a second range of values different from the first range of values.

23 Claims, 4 Drawing Sheets

(56) References Cited

U.S. PATENT DOCUMENTS

| | | |
|---|---|---|
| 2005/0195330 A1* | 9/2005 | Zacks et al. .................. 348/564 |
| 2006/0074321 A1 | 4/2006 | Kouchi et al. |
| 2006/0229557 A1* | 10/2006 | Fathallah et al. ............ 604/131 |
| 2007/0167689 A1* | 7/2007 | Ramadas et al. ............. 600/300 |
| 2007/0180129 A1* | 8/2007 | Tolmie et al. ................ 709/230 |
| 2007/0270669 A1* | 11/2007 | Parnagian .................... 600/301 |
| 2008/0036591 A1* | 2/2008 | Ray .............................. 340/540 |
| 2008/0189173 A1* | 8/2008 | Bakar et al. .................... 705/14 |
| 2009/0002178 A1* | 1/2009 | Guday et al. ............... 340/573.1 |
| 2009/0025022 A1* | 1/2009 | Blatchley et al. ................ 725/9 |
| 2009/0275805 A1* | 11/2009 | Lane et al. .................... 600/300 |
| 2010/0076642 A1* | 3/2010 | Hoffberg et al. ............... 701/29 |

\* cited by examiner

DEVICE AND PROCESS FOR THE OUTPUT OF MEDICAL DATA

CROSS REFERENCE TO RELATED APPLICATIONS

This application claims the benefit of priority under 35 U.S.C. §119 of German Patent Application DE 10 2007 050 060.4 filed Oct. 19, 2007, the entire contents of which are incorporated herein by reference.

FIELD OF THE INVENTION

The present invention pertains to a device and to a process for outputting medical data in a first output mode or in a second output mode different therefrom.

BACKGROUND OF THE INVENTION

A plurality of different outputting means are known for outputting medical data. For example, a monitor may be placed in the vicinity of a hospital bed, an operating table or a treating stool in the field of view of an attending physician, a care provider or a ward nurse, on which a heart rate, blood pressure values and the like of a patient are visually displayed. Likewise, medical data may also be outputted, for example, audibly, e.g., in the form of a sequence of sounds representing the heartbeat. It is also known in such a case, in particular, that medical data can be outputted in the binary form only, by outputting, for example, a warning sound only when certain vital functional parameters are not within preset ranges.

The requirements imposed on the outputting of medical data differ depending on the conditions of use and the ambient conditions. For example, it may be advantageous in a remote monitoring mode to display only a small amount of significant medical data, so that these can be detected at a glance, for example, from a hospital corridor, by a ward nurse passing by. If, by contrast, a physician is treating the patient directly at the hospital bed, a plurality of medical data, for example, also an airway pressure, body temperature, respiration rate or the like shall also be displayed in a close monitoring mode, besides, for example, a heart rate and a blood pressure. Conversely, no warning sound or only a faint warning sound shall be outputted in such a close monitoring mode when a vital function being monitored is critical, whereas a louder alarm sound shall be outputted in the remote monitoring mode, in which no medical staff is usually located in the immediate vicinity of the outputting device.

It may be meaningful under loud hectic or very bright ambient conditions, which frequently prevail, for example, in an emergency admission unit, to output visual and/or audio alarm signals with increased contrast and/or in a brighter form or at a higher volume, while alarm signals shall be outputted at a correspondingly lower volume, with less contrast and/or darker in case of quiet ambient conditions, for example, in an operating room, an intensive care unit or a darkened wake-up room.

It has therefore already been known that different output modes can be used to adapt the output of the medical data to different ambient conditions. For example, in a first output mode, a monitoring screen may be displayed on a monitor, in which only a few numbers are displayed in a very large size, which are also visible from a greater distance. A detail screen with many pieces of information, displayed in a small size, may be displayed in a second output mode, which differs therefrom.

Medical devices frequently have a plurality of different functionalities, which are actuated via only a few input elements. The switchover between different output modes therefore often requires a plurality of operating steps, which are often distributed among different menus. This makes switchover time-consuming and cumbersome and may lead, in particular, to the circumstance that the mode will not be switched back into an initial mode by mistake.

SUMMARY OF THE INVENTION

The object of the present invention is therefore to make available a simple and reliable switchover between different output modes for outputting medical data.

According to the invention, a device is provided for outputting medical data and includes an output means for outputting medical data in at least one first output mode and a second output mode that differs therefrom. The output means may comprise, in particular, a monitor, on which medical data are outputted visually, especially by a symbolic, graphic and/or alphanumeric display, in the first output mode and in the second output mode. The first and second output modes may differ in such a case, for example, concerning brightness, contrast, color, the size of display, the arrangement of the display relative to the monitor and/or a blinking frequency of the display. In addition or as an alternative, the output means may comprise one or more loudspeakers, in which case medical data are outputted in the first and/or second output mode audibly, especially in the form of warning signals or sound sequences representing medical data. The two output modes may differ in this case, for example, concerning loudness and/or tone pitch.

A detection means for detecting an ambient parameter is now provided according to the present invention. Such an ambient parameter may comprise, for example, an ambient brightness and/or an ambient loudness, i.e., it may be equally composed of one or more variables. As will be explained in more detail below, such an ambient parameter may also comprise, in particular, a position of the output means, for example, relative to a reference position, or absolutely, i.e., in space. Thus, different positions of a monitor may differ, for example, relative to an assigned hospital bed or in absolute terms, i.e., they may differ depending on room, floor and the like by an ambient parameter in the sense of the present invention.

Furthermore, an automatic switchover means is provided according to the present invention for outputting the medical data in an output mode. If the ambient parameter detected by the detection means is in a first, preset range of values, the switchover means outputs medical data in the first output mode. If, by contrast, the ambient parameter detected by the detection means is in a second, preset range of values, which differs from the first range, the switchover means outputs medical data in the second output mode.

As a result, an automatic switchover takes place according to the present invention between different output modes depending on the conditions of use and the ambient conditions, which are detected on the basis of an ambient parameter. Switchover can thus be carried out between the different output modes in a simple manner by changing the corresponding ambient parameter in a specific way. If the ambient parameter comprises, for example, the position of a monitor, it is possible to carry out a switchover by shifting the monitor between different output modes.

The switchover advantageously takes place automatically and requires no deliberate separate input. Therefore, if the conditions of use or ambient conditions, which are represented by the ambient parameter, change, a switchover takes place automatically into another output mode, which is more suitable for the new conditions.

For example, in a remote monitoring mode, which is characterized by a monitor position high above a hospital bed, an automatic switchover means according to the present invention may output a small number of significant medical data by large, bright alphanumeric signs, which can also be easily detected at a glance from a hospital corridor from a greater distance by a ward nurse passing by. If an attending physician pulls such a monitor into a lower position in order to have it in his or her field of view during the treatment, an ambient parameter representing the monitor position changes from a first into a second range of values. This can be determined according to the present invention and lead automatically to a switchover into a close monitoring mode, in which a larger number of different medical data are displayed at a lower brightness adapted to viewing from a close range. An ambient brightness or loudness in the vicinity of the output means can likewise be detected as an ambient parameter by a visual or audio sensor and medical data can be outputted by the automatic switchover means with greater contrast or at a higher volume in a first output mode if the ambient parameter is in a first range of values characterizing a brighter or louder environment, whereas medical data are outputted darker or at a lower volume in a second output mode if the ambient parameter is in a second range of values characterizing a darker or lower-volume environment.

According to a first embodiment of the present invention, the output means therefore comprises a monitor, on which medical data are outputted in the first and/or second output mode, especially by a display. The output modes may differ in terms of brightness, contrast, color, display size, arrangement relative to the monitor, blinking frequency and the like. For example, medical data may be displayed in a larger size and/or more brightly in a first mode and in a smaller size and/or darker in a second mode.

In a preferred variant of the first embodiment of the present invention, an input surface is displayed in the first and/or second output mode, by which surface data can be inputted into the device, for example, by means of a touchscreen. While the first output mode is, for example, a monitoring or care mode, in which medical data shall only be displayed, the second output mode may be a data processing mode, in which data can also be inputted via the input surface.

In a second embodiment of the present invention, which may be advantageously combined with the first embodiment, the output means comprises one or more loudspeakers, and medical data are outputted audibly in the first and/or second output mode. The output modes may differ in this case especially in terms of loudness and/or tone pitch. For example, a warning signal can be outputted in a high volume, which is still clearly perceptible even in case of loud disturbing noises, in a loud environment, e.g., in an emergency admission unit or during the operation of loud devices, whereas the same warning signal is outputted at a lower volume in a night rest mode, which is intended for a quiet environment, so that it is essentially perceived by medical staff located in the vicinity of the output means but does not disturb other patients.

The output modes may differ especially concerning the type and/or the number of medical data to be outputted. For example, a small number of significant data, for example, heart rate and/or blood pressure values, can be displayed in a remote monitoring mode, whereas additional detail information, for example, body temperatures, respiration rates, tidal volumes, oxygen saturation and the like are additionally outputted in a close monitoring range.

In an output mode assigned to patient care, it is possible, for example, to suppress an audio alarm signal, which is triggered in a remote or close monitoring mode in case a sensor has fallen off, because sensors frequently fall off in case of patient care.

In a preferred embodiment of the present invention, the output means may comprise two or more output sites, and the output modes differ in terms of the output sites. For example, certain medical values may be outputted in a remote monitoring mode both in the vicinity of a patient being monitored, especially in the vicinity of a hospital bed, as well as remotely therefrom, preferably centrally, for example, in a ward room and/or audibly. Outputting in a ward room is no longer possible in a close monitoring mode, which is usually activated by medical staff present at the patient, so that the medical values are outputted only directly at the hospital bed.

It is equally possible to switch over completely between the output sites, i.e., to output medical data at one of the two output sites only, or to vary the number of output sites, i.e., to output medical data in different output modes at a different number of output sites only. The medical values being outputted may differ depending on the output mode and/or the output site.

An ambient parameter in the sense of the present invention may comprise one or more values, which characterizes/characterize a use situation or an ambient situation. It may comprise, for example, an ambient brightness, expressed, for example, in Lux, candela or the like, and/or an ambient loudness, expressed, for example, in phon or sone. The detection means may have for this correspondingly one or more visual sensors for detecting the brightness or audio sensors for detecting the loudness. A first or second range of values can then be defined by presetting certain minima and/or maxima for the brightness or the loudness.

In addition or as an alternative, an ambient parameter may also comprise a Position of the output means. It may be a relative position of the output means, i.e., relative to a reference position. If the output means is arranged, for example, on an adjustable, especially pivotable articulated arm, the relative or reference position can be represented by degrees of freedom of the articulated arm, especially its articulation angle, i.e., the ambient parameter may comprise the position, configuration or pose of one end of the articulated arm. With respect to another end. A first or second range of values can then be defined by presetting minimal and/or maximum deviations from reference articulation angles. If the articulated arm comprises translatory or linear articulations, the ambient parameter may, of course, also comprise deviations of the current position from a reference position in the linear articulations.

The ambient parameter does not have to comprise all degrees of freedom of an articulated arm. In particular, two ranges of values may differ, for example, by a single pivot angle of the articulated arm, which differentiates a position which is a position pivoted towards a hospital bed in one monitoring mode from a position which is a position pivoted away from the hospital bed in a care mode.

In addition or as an alternative, the absolute position of the output means may also be used as an ambient parameter, for example, the positioning of the output means within a hospital. Thus, the switchover means can switch over into a remote monitoring mode when a mobile output means is located in a patient room and into a close monitoring mode when the output means is in an operating room.

Different situations of use are frequently characterized by different levels and/or distances from a wall of an output means. For example, a monitor for remote monitoring is frequently positioned relatively high and/or close to a wall of a room. The same monitor is pulled for close monitoring to a lower operating level with a greater distance from a wall. For patient care or for data processing, such a monitor may, in turn, be brought to another level or to another distance from a wall. Ranges of values can therefore also be defined by minimal and/or maximal distances between the output means and one or more reference planes, for example, in case of redundant articulated arms also independently from the degrees of freedom that define a distance. For example, a first range of values, assigned to remote monitoring, may be defined, for example, by a minimum distance of 150 cm between the output means and the floor level in a preferred embodiment, and a second range of values, assigned to close monitoring, may be defined by a distance between 120 cm and 150 cm between the output means and the floor. A third range of values, assigned to data processing, may be defined by a maximum distance of 120 cm between the output means and the floor level.

As it becomes clear especially from this, the present invention is not limited to output in two different output modes. The switchover means can rather switch over in a preferred embodiment of the present invention automatically into a third output mode different from the first and second output modes if the ambient parameter detected by the detection means is in a third range of values different from the first and second ranges of values. It is preferably also possible to provide additional output modes and corresponding ranges of values.

Other advantages and features of the present invention appear from the exemplary embodiments described below. This is shown in the drawings in a partly schematic form. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF THE PREFERRED EMBODIMENTS

Figure 1:
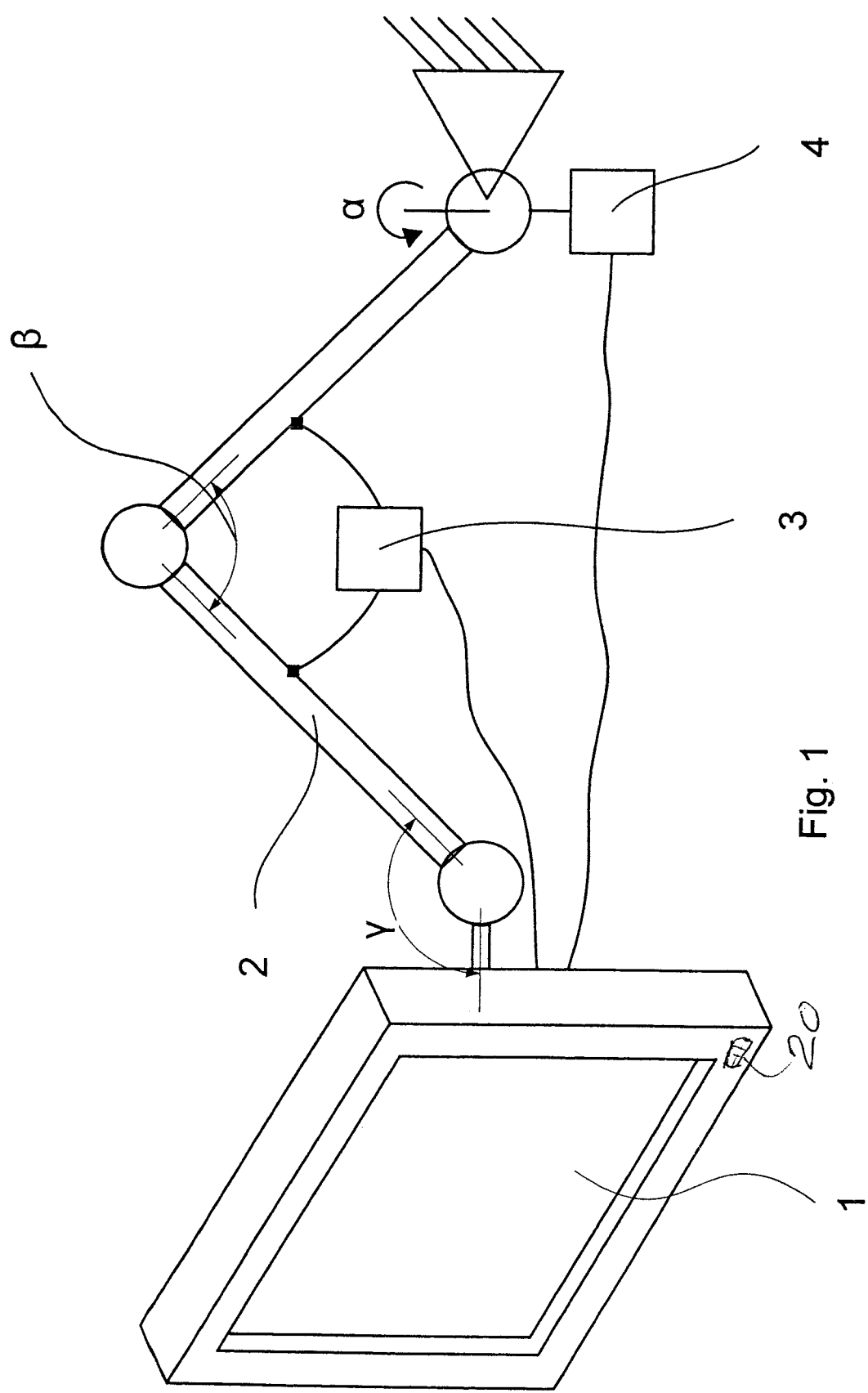
FIG. 1 is a perspective view showing a device for outputting medical data according to a first embodiment of the present invention.

Referring to the drawings in particular, FIG. 1 shows a device for outputting medical data according to a first embodiment of the present invention, which is intended for carrying out a process according to an embodiment of the present invention. The device comprises an outputting means, or broadcaster, in the form of a monitor 1, which is arranged on an articulated arm 2 in a level-adjustable and pivotable manner. One end of the arm 2 with respect to another end of the arm 2 can be pivoted for this in a first, inertial mounting joint about an angle α about a vertical axis and in a second and third joint following the first joint about a horizontal axis each about an angle β and γ, respectively.

The detection means for detecting an ambient parameter comprises a first angle of rotation sensor 3 for detecting the angle β of the middle joint of the articulated arm 2 in relation to a horizontal and a second angle sensor 4 for detecting the angle of rotation α about the vertical axis. The two angles α, and β form together the ambient parameter and are transmitted to an automatic switchover means, which is integrated in monitor 1 (not shown).

The device is arranged stationarily in a patient room in the vicinity of a patient bed (not shown). Medical data of a patient located in the patient bed, for example, the heart rate, blood pressure values of the patient and the like, can be displayed on the monitor. Monitor 1 is connected for this to corresponding monitoring sensors for detecting medical data (not shown).

In addition, the outputting means comprises another monitor (not shown), which is connected just like monitor 1 and is arranged in a ward room.

In a first output mode, which is intended for remote monitoring, only the heart rate and the systolic and diastolic blood pressures are displayed on monitor 1 in the form of numbers measuring 70 mm in height, for example, in white or blue color. The same medical values are also displayed on the monitor situated in the ward room.

If the medical value of the patient, which is being monitored, moves outside a preset range of values, a visual alarm is triggered on monitor 1 by an alarm light (not shown) blinking, and the medical data that have moved outside the normal range and triggered the alarm are displayed in addition to the above-mentioned medical data. If, for example, an oxygen saturation has dropped below a preset limit of 85%, the current $SpO_2$ value is likewise displayed in large letters, readily legible from a greater distance, but in an alarm color, for example, red.

An alarm light is also activated on the monitor in the ward room and the medical data triggering the alarm are additionally displayed in signal color. In addition, an audio warning signal is sent via a loudspeaker (20) integrated in the monitor in the ward room.

In a second output mode, which is intended for close monitoring, a detail view, which can be configured by a user and which comprises, for example, curves for the first to third leads of an ECG, invasive blood pressure values, an airway pressure, respiration flow, plethysmogram, heart rate, ST depression, peak and mean values for the blood pressure, a body temperature, spontaneous respiration rate and spontaneous tidal volume and/or an oxygen saturation, is displayed on monitor 1. The individual medical data are displayed for this in smaller letters and diagrams. In addition, a keyboard, by means of which lower menu levels of the devices can be selected via the monitor 1 designed as a touchscreen, is displayed in the second output mode.

An alarm is also triggered in the patient room in the second output mode both visually and audibly by outputting an alarm tone in addition to the blinking alarm light and specific alarm report described above with reference to the first output mode via a loudspeaker 20 integrated in monitor 1. In addition, specific alarm reports can be displayed.

The outputting of the medical data on the monitor in the ward room corresponds to the manner described with reference to the first output mode.

The ECG curve as well as the heart rate, the respiratory minute volume and tidal volume as well as the oxygen saturation are displayed on monitor 1 in a third output mode, which is intended for patient care, because other parameters are often distorted during care treatments.

It may happen during such care treatments that sensors for monitoring medical data are interrupted or fall off. Sensors that have been interrupted or have fallen off are therefore displayed only visually on monitor 1 in the third output mode, but, contrary to the first and second output modes, no audio warning signal is outputted either in the patient room or in the ward room.

Analogously to the fading in of the keys for accessing lower menu levels of the device in the second output mode, keys are displayed in the third output mode for patient care for starting certain maneuvers, RSVT (re-entrant supraventricular tachycardia) or measurement of the cardiac minute volume, via which the corresponding maneuver can be started by means of the touchscreen of monitor 1.

In a fourth output mode, which is intended for data processing, a view in which it is possible to switch over between data management programs used by the user or the like is displayed on monitor 1. The above-described hemodynamic parameters and curves are faded out in the display except for a small window, in which the ECG curve, a numeric heart rate value as well as optionally alarms are displayed. An audio alarm by loudspeaker in monitor 1 is switched off here as well, as long as the monitor is operated or moved within a time window of 120 sec.

If no medical staff is located in the vicinity of the patient, the patient's status shall be able to be rapidly recognized from a greater distance, for example, while passing by the door of the room. The monitor is raised for this by rotating in the second and third joints until a lower edge of the display screen is 150 cm or more above the floor level of the room. It can be readily recognized even from a greater distance in such a position.

If monitor 1 assumes the above-described position, the articulation angle $\beta$ is within a first range of values, which depends on the geometry of the articulated arm 2, especially the lengths of the members and the level of the first joint, and which is defined by a lower limit $\beta$min. The angle of rotation sensors 3, 4 monitoring the articulation angles $\alpha$, $\beta$ detect the articulation angles $\alpha$, $\beta$ as ambient parameters ($\alpha$, $\beta$) and pass this on to the automatic switchover means in monitor 1. The automatic switchover means recognizes on the basis of the angle of rotation $\beta$>$\beta$min, which is within the first range of values, that monitor 1 is in a position intended for remote monitoring. It therefore outputs the medical data in the above-described first output mode, i.e., it displays only few numbers in a large size, and an audio alarm is triggered in the center only.

If medical staff, for example, an attending physician, is at the bedside and would like to read detail information on the monitor 1 in the close monitoring mode, the user pulls the monitor 1 to an operating level between 120 cm and 150 cm, in which case the articulation angle $\alpha$ relative to the wall is between 80° and 110°. The second range of values assigned to close monitoring is therefore defined such that the ambient parameter formed by the articulation angles $\alpha$, $\beta$ is in the second range of values when angle $\alpha$ about the vertical axis is in a range between 80° and 110° and the angle of rotation $\beta$ of the middle joint is in an angle range that corresponds, depending on the geometry of the articulated arm, to an operating level between 120 cm and 150 cm.

The angle of rotation sensors 3, 4 monitoring the ambient parameter transmit the ambient parameter ($\alpha$, $\beta$) to the automatic switchover means, which correspondingly outputs medical data in the second output mode intended for close monitoring when the ambient parameter, i.e., the two articulation angles $\alpha$, $\beta$, is within the second range of values explained above.

If the medical staff wants to perform care treatments on the patient, monitor 1 is pivoted about its vertical axis of rotation towards the patient, so that the articulation angle $\alpha$ in relation to the wall is smaller than 80°. Monitor 1 can now be viewed from both sides of the bed and from the head end. Contrary to a remote monitoring position, monitor 1 is not, however, at least 150 cm above the floor level.

A third range of values assigned to patient care is therefore defined in that the angle of rotation $\alpha$ is smaller than 80°, while angle $\beta$ is below the lower limit $\beta$min, which was explained above and represents a monitor level above 150 cm. If the angle of rotation sensor 4 transmits a corresponding angle of rotation $\alpha$<80°, $\beta$<$\beta$min to the automatic switchover means, the latter will recognize that a patient care is being carried out and outputs medical data in the above-described third output mode assigned to patient care, i.e., it displays selected parameters only and mutes an audio alarm.

To prevent the switchover means from continuously outputting data unintendedly in the third output mode, i.e., especially without audio alarming in case of sensors that have been interrupted or have fallen off, when one forgot to move the monitor 1 back into a close or remote monitoring position, the automatic switchover means will automatically output medical data again in the first output mode assigned to remote monitoring if a preset time has elapsed without monitor 1 having been operated or its positioned changed.

If the medical staff wants to use the monitor to work with a data processing program or the like, monitor 1 is pulled to a working level for data input, in which a lower edge of the screen is at least 120 cm above the floor level and an angle $\alpha$ in relation to the wall is greater than 80°. A fourth range of values assigned to data processing is correspondingly defined by the first articulation angle $\alpha$ being greater than 80° and by the middle articulation angle $\beta$ being below a maximum $\beta$max preset by the geometry of the articulation arm 2, which corresponds to a display screen level of less than 120 cm.

If corresponding angles of rotation $\alpha$, $\beta$ are detected by the detection means 3, 4 and transmitted as an ambient parameter to the automatic switchover means, the latter will recognize that the ambient parameter is in the fourth range of values assigned to data processing and outputs medical data in the fourth output mode explained above, which is assigned to data processing, i.e., it displays the ECG curve and the heart rate value as well as optionally alarms in a small window only.

In the first embodiment, the ambient parameter comprises the two articulation angles $\alpha$, $\beta$. If angle $\alpha$ about the vertical axis is now between 80° and 110° and angle $\beta$ about the horizontal axis is in a range that corresponds—as a function of the level at which the articulated arm 2 is mounted above floor level and the lengths of the members of the articulated arm 2—to a monitor operating level of 120 cm to 150 cm above the floor level, the ambient parameter is in the second range of values assigned to close monitoring. If angle $\alpha$ is greater than 80° and angle $\beta$ is smaller than a maximum angle $\beta$max, which corresponds, in turn, depending on the geometry of the articulated arm 2, to a level of the lower edge of the screen of monitor 1 equaling 120 cm above floor level, the ambient parameter is in the fourth range of values assigned to data processing. If monitor 1 is pivoted about to the patient bed, i.e., the angle $\alpha$ in relation to the wall is less than 80°, while the articulation angle $\beta$ is less than the angle $\beta$min representing the screen level of 150 cm, the ambient parameter is in the third range of values assigned to patient care. If angle $\beta$ is greater than the minimum angle $\beta$min, which corresponds to a level of the lower edge of the screen of monitor 1 equaling 150 cm above floor level, the ambient parameter $\alpha$, $\beta$ is in the first range of values assigned to remote monitoring for all pivot angles $\alpha$. If, finally, angle $\alpha$ about the vertical axis is greater than 110° and angle $\beta$ is at the same time in a range that corresponds to a monitor operating level between 120 cm and 150 cm above floor level, the ambient parameter is in a first range of values, due to which the automatic switchover means outputs medical data in a first output mode assigned to a sleep mode, in which only medical data that are outside a preset normal value are outputted.

Figure 2:
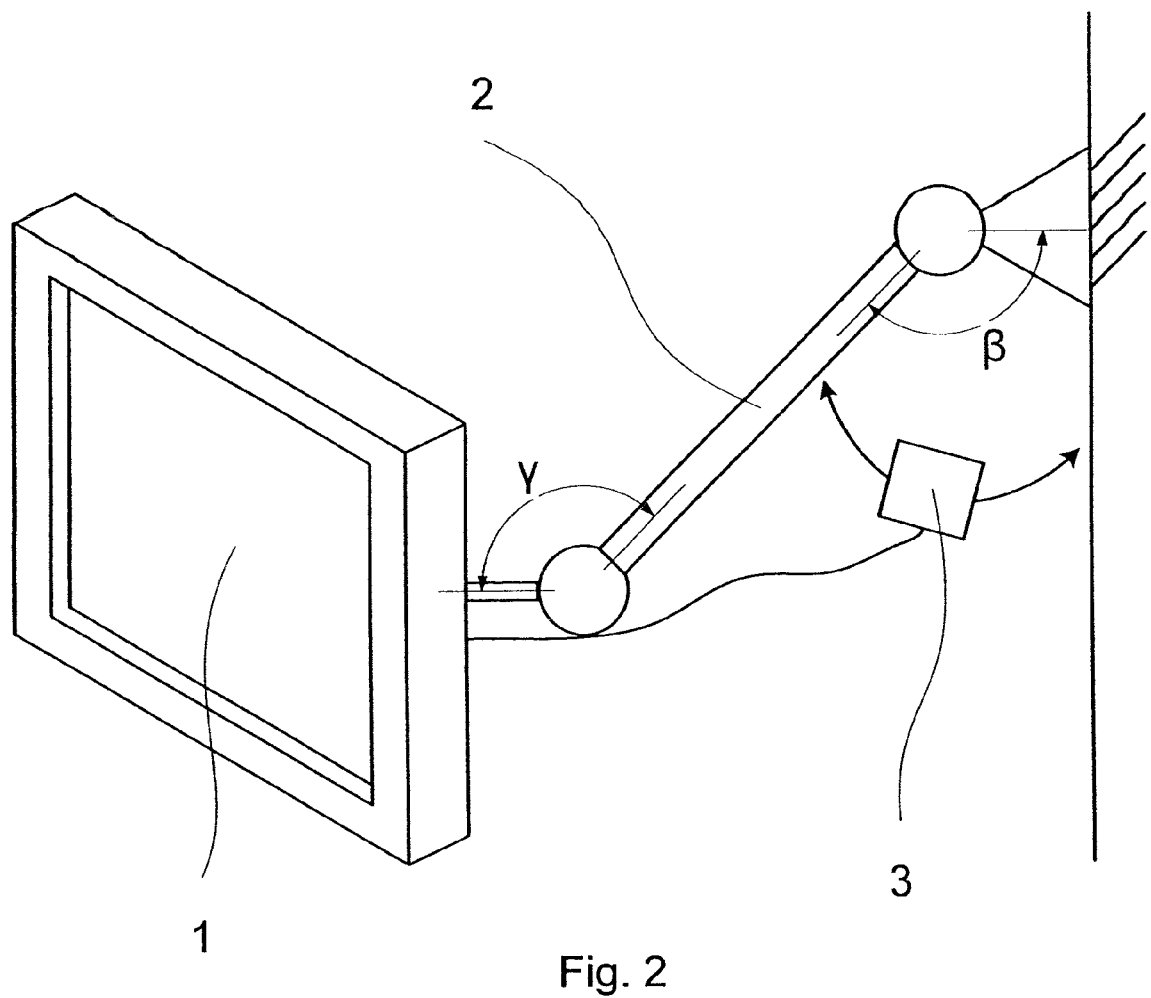
FIG. 2 is a perspective view showing a device for outputting medical data according to a second embodiment of the present invention.

FIG. 2 shows a device according to a second embodiment of the present invention. Elements and features corresponding to the first embodiment are designated by identical reference numbers, so that reference is made in this connection to the explanations given above and only the differences from the first embodiment will be dealt with below.

The articulated arm 2 of the device according to the second embodiment of the present invention is adjustable in level in a simple manner only, and it has two hinges for this, which make possible rotation by the angle $\beta$ or $\gamma$ about a horizontal axis.

The detection means comprises only a contact switch 3, which outputs a signal to the automatic switchover means if monitor 1 is positioned above a predetermined level. If, for example, the articulated arm 2 is mounted inertially at a level of 1 m above floor level and the first member of the articulated arm 2, which said member is rotatable by the angle $\beta$, has a length of 1 m, the contact switch 3 is set such that at an angle $\beta$ of the first member of the articulated arm 2 of at least 30° in relation to the horizontal, it outputs a signal to the automatic switching means that indicates that the ambient parameter $\beta$ is in the first range of values. The automatic switchover means recognizes from this that a lower edge of the screen of monitor 1 is at least 150 cm above floor level and it outputs medical data in the first output mode described in reference to the first embodiment for remote monitoring, i.e., it displays the heart rate and the blood pressure in large numbers in a neutral color, while an alarm is generated only by the loudspeakers in the monitor in the ward room. If, by contrast, angle $\beta$ is smaller than 30°, contact switch 3 outputs no signal to the automatic switchover means, which recognizes from this that the monitor shall not be used for remote monitoring and outputs medical data in the second output mode described with reference to the first embodiment for close monitoring, i.e., it displays a detail view and optionally also generates an audio alarm.

The ambient parameter therefore comprises only the articulation angle $\beta$ in the second embodiment, and the first range of values assigned to remote monitoring comprises all values $\beta \geq 30°$, and the second range of values assigned to close monitoring comprises all other values of $\beta$.

Figure 3:
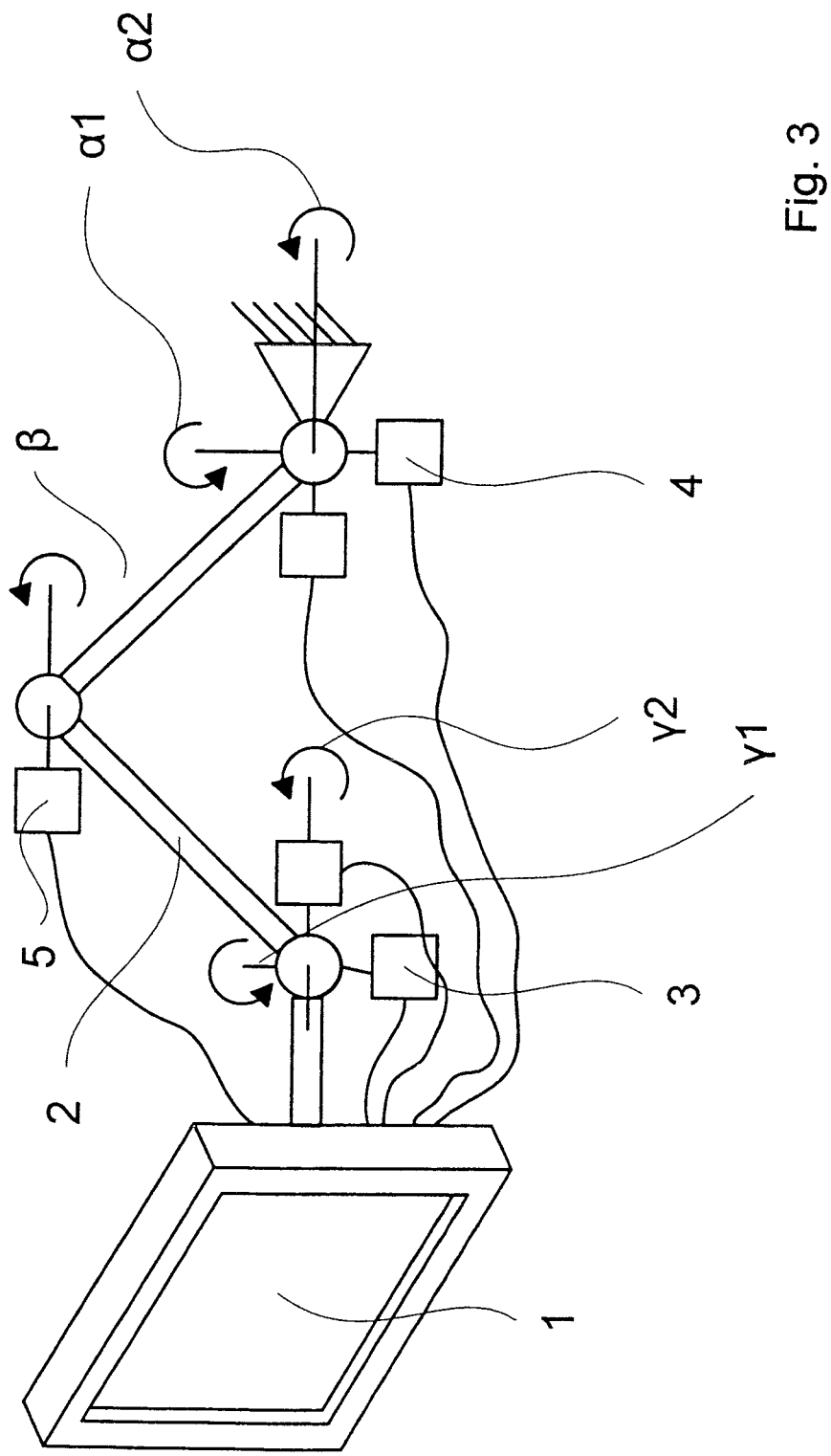
FIG. 3 is a perspective view showing a device for outputting medical data according to a third embodiment of the present invention.

FIG. 3 shows a third embodiment of the present invention, wherein elements and features corresponding to each other in reference to the first and second embodiments are again designated by identical reference numbers, so that reference is also made in this respect to the explanations given in connection with the first and second embodiments, and only the differences in the third embodiment will be dealt with below.

The first, inertial joint and the last joint of articulated arm 2, on which monitor 1 is mounted, are designed as a ball and socket joint each in the third embodiment, whereas the middle joint makes possible, as before, rotation about the horizontal axis only.

Corresponding to this, angle sensors 3, 4 for the first and last hinge, respectively, detect an angle $\alpha 1$ and $\gamma 1$ of the next member of the articulated arm 2 about a vertical axis and an angle $\alpha 2$ and $\gamma 2$, respectively, of the next member against the horizontal. Angle sensor 5 detects angle $\beta$ of the second member of the articulated arm 2 in relation to the first, inertially mounted member.

Monitor 1 of the third embodiment of the present invention can be positioned in additional positions, i.e., locations and/or orientations in relation to the first embodiment based on the additional degrees of freedom of the articulated arm 2. The ranges of values can correspondingly also be differentiated more finely and/or additional ranges of values can be defined. For example, the first range, which was explained with reference to the first embodiment and is assigned to remote monitoring, may be defined such that the ambient parameter comprising the angles of rotation $\alpha 1$, $\alpha 2$, $\beta$, $\gamma 1$ and $\gamma 2$ is within the first range of values if monitor 1 is sloped by more than 5° in relation to the horizontal ($\gamma 2 > 5°$), because such a downward slope of monitor 1 occurs during remote monitoring only, during which the monitor 1 is positioned above the level of the head.

Figure 4:
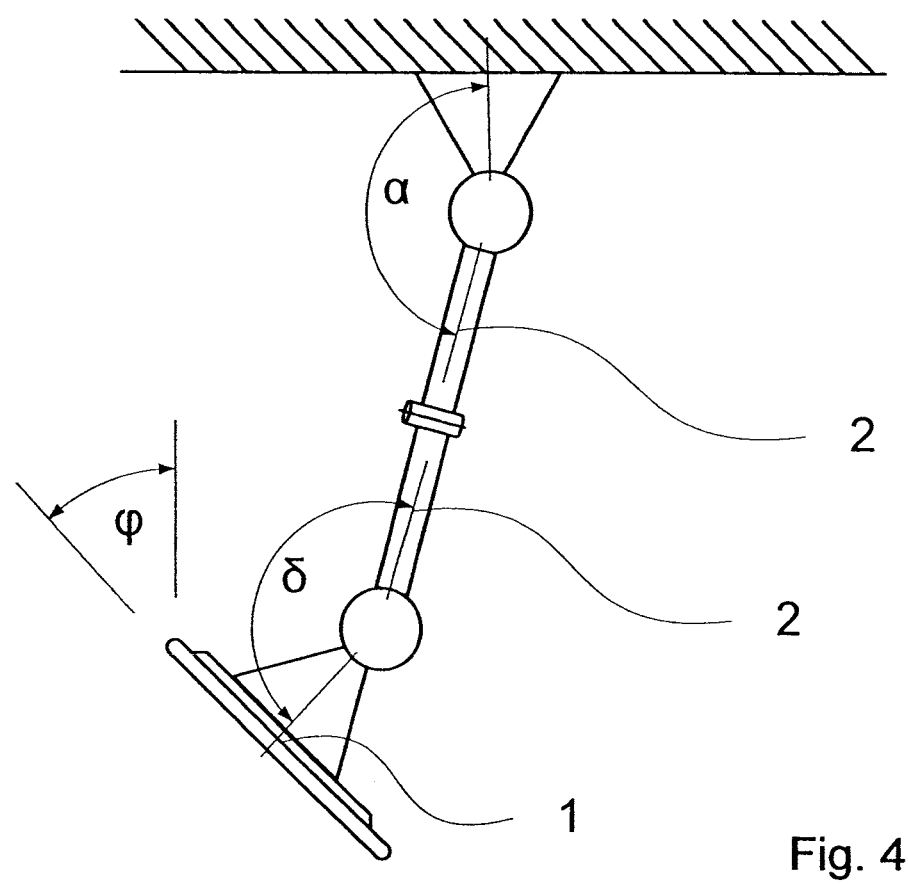
FIG. 4 is a top view of a device for outputting medical data according to a fourth embodiment of the present invention.

FIG. 4 shows a top view of a fourth embodiment of the present invention. The articulated arm 2 is fastened in this embodiment in a first hinge vertically pivotably at the wall (top in FIG. 4), and a pivot angle of the articulated arm 2 about the vertical axis in the inertial bearing in relation to a position that is at right angles to the wall is defined by the angle of rotation $\alpha$. Monitor 1 is mounted at the other end of the articulated arm 2 in a hinge, which makes possible pivoting about a vertical axis, $\delta$ representing the angle of the monitor 1 in relation to a position in which its display screen is oriented at right angles to the longitudinal axis of articulated arm 2.

Angle $\phi$ of the display screen in relation to an orientation at right angles to the wall forms an element of the ambient parameter in the fourth embodiment. To determine it, angle sensors (not shown) measure the articulation angles $\alpha$ and $\delta$, from which the detection means determines the angle $\phi$ by addition to 90° ($\phi = 90° + \alpha + \delta$) if $\alpha$, $\delta$ and $\phi$ are each measured mathematically in the positive direction counterclockwise.

An audio sensor, not shown, detects a loudness of the ambient noise, which likewise forms an element of the ambient parameter.

A first range of values assigned to remote monitoring is now defined for all angles $\phi$ by the loudness of the ambient noise, $\lambda$, being below a defined minimum $\lambda$min corresponding to a quiet patient room. Therefore, if the audio sensor detects that it is quiet in the patient room, the automatic switchover means always outputs medical data in the first output mode explained with reference to the first exemplary embodiment, which is assigned to remote monitoring.

If, by contrast, the loudness of the ambient noise, $\lambda$, is above the minimum $\lambda$min, a further differentiation is made corresponding to angle $\phi$.

If monitor 1 is pivoted towards the patient bed, so that the angle $\phi$ is lower than 80°, the automatic monitoring means recognizes that the ambient parameter ($\lambda$, $\phi$) is in the third range of values ($\lambda > \lambda$min; $\phi < 80°$), which is assigned to patient care, and outputs medical data in the third output mode assigned to patient care, which is described with reference to FIG. 1. If, by contrast, the angle $\phi$ determined from the measured articulation angles $\alpha$, $\delta$ is in a second range between 80° and 110°, the ambient parameter is in a second range of values ($\lambda > \lambda$min; $80° < \phi < 110°$), and the automatic monitoring means outputs medical data in the second output mode assigned to close monitoring, which is described with reference to the first embodiment. If, by contrast, angle $\phi$ is greater than 110°, i.e., the ambient parameter is in a fourth range of values ($\lambda >$min; $\phi > 110°$), the automatic monitoring means outputs medical data in a fourth output mode assigned to data processing, which corresponds to the fourth output mode described with reference to the first embodiment.

In a fifth embodiment, not shown, of the present invention, the output means comprises a loudspeaker for outputting medical data in the audio form, which comprise an audio pulse signal as well as an audio alarm signal, if the heart rate of a patient being monitored is outside a preset normal range. The detection means comprises a characteristic sensor for detecting an ambient noise loudness as the ambient parameter.

If this is within a first range of values, which is limited upwards by a maximum loudness, which corresponds to a patient room during undisturbed night rest, the automatic switchover means outputs the medical data in a first output mode, in which only the audio alarm signal is outputted with the normal loudness, if the heart rate of a patient being monitored moves outside the preset normal range. If the ambient noise loudness is within a third range of values, which is limited downwards by a minimum loudness, which corresponds to a patient room during emergency operation or a noisy environment, as is generated, e.g., by an active pneumatic surgical drill, the automatic switchover means outputs the medical data in a third output mode, in which both the audio pulse signal and the audio alarm signal are outputted with an increased loudness, which is clearly perceptible even in a noisy environment. If, finally, the ambient noise volume is within a second range of values, which is limited upwards and downwards by the maximum loudness and the minimum loudness and corresponds to a hospital room in a normal environment, the automatic switchover means outputs the medical data in a second output mode, in which both the audio pulse signal and the audio alarm signal are outputted with a lower volume, which is perceptible in normal environment.

In the fifth embodiment, not shown, the ranges of values are thus distinguished according to the ambient noise volumes detected as an ambient parameter, and the associated output modes differ both according to the number and the volume of the medical data being outputted in the audio form.

While specific embodiments of the invention have been shown and described in detail to illustrate the application of the principles of the invention, it will be understood that the invention may be embodied otherwise without departing from such principles.

| List of Reference Numbers | |
|---|---|
| 1 | Monitor |
| 2 | Articulated arm |
| 3, 4, 5 | Articulation angle sensor |
| α, α1, α2, β, γ1, γ2, δ | Articulation angles |
| φ | Monitor angle |

What is claimed is:

1. A device for the output of medical data of a patient, the device comprising:
an adjustable articulated arm having a first end and a second end, said second end being movable into a plurality of output positions with respect to said first end;
a plurality of monitoring sensors for detecting medical data of the patient, said monitoring sensors being connected to said medical data output device;
a medical data output means for providing an output of medical data in a first output mode or in a second output mode, said first output mode having a smaller data form than a data form of said second output mode, said medical data output means being arranged on said second end of said adjustable articulated arm, and movable into a plurality of output positions with respect to said first end of said arm, said plurality of output positions including a close range and a remote range, said close range including one of said output positions being closer to the patient than one of said output positions in said remote range;
a detection means for detecting said plurality of output positions of said output means relative to said first end of said arm; and
an automatic switch over means for outputting medical data in a first output mode if output position detected by said detection means is in said close range, and for outputting medical data in a second output mode if said output position detected by said detection means is in said remote range, said close range of values being closer to the patient than said remote range.

2. A device in accordance with claim 1, wherein:
said output means comprises a monitor; and
a larger number of medical data are output in said first output mode than in said second output mode.

3. A device in accordance with claim 2, wherein the first output mode and the second output mode differ in terms of arrangement of data relative to the monitor and/or blinking frequency.

4. A device in accordance with claim 2, wherein:
said plurality of output positions include an intermediate range, said intermediate range including one of said output positions being arranged between said close range and said remote range;
an input surface is displayed on said medical data output device when said output position is in said intermediate range, said input surface not being displayed when said output position is in said remote range.

5. A device in accordance with claim 1, wherein:
said medical data output means comprises a loudspeaker; and
medical data are provided as output in the first and second output modes audibly, including a medically indicated warning signal, said audio output being lower when said output position is in said close range than when said output position is in said remote range.

6. A device in accordance with claim 5, wherein the first and second output modes differ in terms of tone pitch.

7. A device in accordance with claim 1, wherein the medical data in said first mode comprise a blood pressure, especially an arterial central venous and/or pulmonary invasive arterial peak and/or mean blood pressure value, an oxygen saturation, electrocardiogram data, especially a first through third lead, an airway pressure, a respiration flow, a plethysmogram, a heart rate, an ST depression, a body temperature, a spontaneous respiration rate and a spontaneous tidal volume.

8. A process for outputting medical data of a patient by means of a device, the process comprising the steps of:
providing an adjustable arm with a medical data output device on one end of the arm;
providing a plurality of monitoring sensors for detecting medical data of the patient, said monitoring sensors being connected to said medical data output device;
moving said medical data output device into a plurality of different output positions with respect to another end of the adjustable arm, said plurality of output positions including a close range and a remote range, said close range being closer to the patient than said remote range;
detecting the plurality of output positions of said output device relative to said first end of said adjustable receiving a plurality of medical data streams from said monitoring sensors at said medical data output device;

selectively broadcasting data from the medical data streams in a plurality of different data forms on said medical data output device, said plurality of different data forms including a close monitoring mode and a remote monitoring mode, said close monitoring mode displaying medical data in a smaller size than said remote monitoring mode displays medical data, said broadcasting of medical data displaying the medical data in said close monitoring mode when said output position is in said close range, said broadcasting of medical data displaying the medical data in said remote monitoring mode when said output device is in said remote range.

9. A device in accordance with claim 1, wherein:
said detection means comprises one or more angular and/or linear sensors for detecting a position of said articulated arm;
said automatic switch over means is connected to said medical output means and said detection means.

10. A device for displaying medical data of a patient, the device comprising:
an adjustable arm having a first end and a second end, said second end of said adjustable arm being movable into a plurality of output positions relative to said first end, said plurality of output positions including a close range and a remote range, said close range including one of said output positions being closer to the patient than one of said output positions in said remote range, said first end of said arm is a base arranged at a fixed location;
an output device for broadcasting data in a one of a visual and audio media, said output device receiving a plurality of different data streams, said output device selectively broadcasting the data in a plurality of different data forms, said plurality of different data forms including a close monitoring mode and a remote monitoring mode, said close monitoring mode displaying medical data in a smaller size than said remote monitoring mode displays medical data, said output device being arranged on said second end of said adjustable arm and movable into a plurality of output positions by said adjustable arm relative to said first end of said adjustable arm;
a plurality of monitoring sensors for detecting medical data of the patient, said monitoring sensors being connected to said medical data output device;
a detector connected to said output device and detecting said plurality of output positions of said output device relative to said first end of said adjustable arm;
an automatic switch connected to said output device and said detector, said automatic switch displaying the medical data in said close monitoring mode when said output position is in said close range, said automatic switch displaying the medical data in said remote monitoring mode when said output position is in said remote range.

11. A process in accordance with claim 8, wherein:
said detecting is performed by one or more angular and/or linear sensors for detecting the configuration of the arm.

12. A process in accordance with claim 8, wherein:
said first end of said arm is a base arranged at a fixed location.

13. A process in accordance with claim 8, wherein:
said close range is lower than said remote range.

14. A process in accordance with claim 8, wherein:
said close monitoring mode displays a larger number of parameters than said remote monitoring mode.

15. A process in accordance with claim 8, wherein:
said plurality of output positions include an intermediate range, said intermediate range being arranged between said close range and said remote range;
said medical data output device includes an input surface, said input surface being activated when said output device is in said intermediate range, said input surface being deactivated when said output device is in said remote range.

16. A process in accordance with claim 8, wherein:
said medical data output device includes an audio output broadcasting medical data in an audio form, said audio output being lower when said output device is in said close range than when said output position is in said remote range.

17. A process in accordance with claim 16, wherein:
said audio output is in a different pitch when said output device is in said close range than when said output device is in said remote range.

18. A process in accordance with claim 8, wherein:
said broadcasting of medical data displaying the medical data in said close monitoring mode when said medical data output device is in an operating room, said broadcasting of medical data displaying the medical data in said remote monitoring mode when said medical data output device is in a patient room.

19. A device in accordance with claim 10, wherein:
one of said plurality of output positions in said close range is lower than one of said plurality of output positions in said remote range;
said close monitoring mode displays a larger number of parameters than said remote monitoring mode.

20. A device in accordance with claim 10, wherein:
said plurality of output positions include an intermediate range, said intermediate range including one of said output positions being arranged between said close range and said remote range;
said output device includes an input surface, said input surface being activated when said output position is in said intermediate range, said input surface being deactivated when said output position is in said remote range.

21. A device in accordance with claim 10, wherein:
said output device includes an audio output broadcasting medical data in an audio form, said audio output being lower when said output position is in said close range than when said output position is in said remote range.

22. A device in accordance with claim 21, wherein:
said audio output is in a different pitch when said output position is in said close range than when said output position is in said remote range.

23. A device in accordance with claim 10, wherein:
said output device displays the medical data in said close monitoring mode when said output device is in an operating room, said output device displays the medical data in said remote monitoring mode when said output device is in a patient room.

* * * * *